(12) United States Patent  (10) Patent No.: US 7,843,351 B2
Bourne et al.  (45) Date of Patent: Nov. 30, 2010

(54) BACK TRAINING DEVICE

(76) Inventors: Robert Bourne, 5130 Cottonwood La., Salt Lake City, UT (US) 84117; Lorenzo Hyland, 2792 Morgan Dr., Salt Lake City, UT (US) 84124

(*) Notice: Subject to any disclaimer, the term of this patent is extended or adjusted under 35 U.S.C. 154(b) by 1244 days.

(21) Appl. No.: 10/931,798

(22) Filed: Sep. 1, 2004

(65) Prior Publication Data
US 2006/0047232 A1  Mar. 2, 2006

(51) Int. Cl.
*G08B 23/00* (2006.01)
*A61B 5/103* (2006.01)
*A61B 5/00* (2006.01)

(52) U.S. Cl. .................. 340/573.7; 340/573.1; 600/595; 73/865.4

(58) Field of Classification Search ............. 33/512, 33/511; 434/247; 600/595; 482/3–9, 900–903; 340/573.1, 573.7; 73/865.4
See application file for complete search history.

(56) References Cited

U.S. PATENT DOCUMENTS

| 4,665,928 | A  | * | 5/1987  | Linial et al. .............. 600/595 |
| 5,398,697 | A  | * | 3/1995  | Spielman .................. 600/594 |
| 5,474,083 | A  | * | 12/1995 | Church et al. ............ 600/546 |
| 5,749,838 | A  | * | 5/1998  | Kline ........................ 601/71 |
| 6,059,576 | A  | * | 5/2000  | Brann ....................... 434/247 |
| 6,682,351 | B1 | * | 1/2004  | Abraham-Fuchs et al. .. 434/247 |
| 7,028,547 | B2 | * | 4/2006  | Shiratori et al. ............ 73/495 |
| 7,141,026 | B2 | * | 11/2006 | Aminian et al. .......... 600/595 |
| 7,198,607 | B2 | * | 4/2007  | Jamsen ..................... 600/595 |
| 7,330,760 | B2 | * | 2/2008  | Heruth et al. .............. 607/17 |
| 7,395,113 | B2 | * | 7/2008  | Heruth et al. ............... 607/3 |
| 2002/0170193 | A1 | * | 11/2002 | Townsend et al. .......... 33/512 |

* cited by examiner

*Primary Examiner*—Loan Thanh
*Assistant Examiner*—Sundhara M Ganesan
(74) *Attorney, Agent, or Firm*—Workman Nydegger (57) ABSTRACT

A novel back training device is disclosed. The back training device includes a control box; a detector mounted to the control box, for detecting when a person bends at the waist; and an alert means, operatively connected to the detector for alerting the person when the person bends at the waist.

62 Claims, 5 Drawing Sheets

BACK TRAINING DEVICE

FIELD OF THE INVENTION

The present invention is directed to the field of lower back motion sensing devices that monitors unsafe spinal movement. In particular, the present invention helps individuals to re-train themselves to bend primarily at the knees instead of bending primarily at the waist by using biofeedback technology and Pavlovian response.

BACKGROUND OF THE INVENTION

The present invention employs a sensor that detects whether its user is bending at the waist beyond a certain set point and warns the user through a vibrating, shocking, or audible alarm. The present invention is attached to the user through a novel cloth belt, narrow strap, plastic holster with a belt clip (like the ones that hold pagers) onto a person's belt, or adhesive patch.

U.S. Pat. No. 5,398,697 is directed to a spinal monitor, which detects movements of the lower back in lifting, bending and twisting through the use of a modified "t"-shaped collimated light beam emitted from a unit worn at the base of the spinal column and detected along the column as long as the spinal motion is within prescribed limits of flexion, extension, and left and right lateral movements—and beyond which an audible signal alert is provided as a warning of unsafe spinal movement.

U.S. Pat. No. 5,474,083 discloses a microprocessor based system utilizing electromyographic sensor to monitor muscle force for lift training and exercise training. In the lift training embodiment the electrodes of the electromyographic sensor are secured to a belt so that they are located adjacent to the lower back of the user when wearing the belt. The lift training embodiment is also provided with a goniometer to measure lifting angle during training, which together with muscle force generated by the lower back is compared in the microprocessor to a programmed lifting parameters and if these parameters are exceeded the user is warned by an audible indicator. The lift trainer embodiment also periodically measures interelectrode impedance to insure actual usage. The exercise training embodiment has a bar graph display displaying muscle intensity and two light emitting diodes alerting a user when to contract or relax a monitored muscle group. The microprocessor is programmed with a exercise routine and alerts a user when the routine is to begin, the duration of muscle contraction and relaxation, and the repetitions required. During exercise the user can monitor muscle intensity from the bar graph display and or auditory feedback element. An alternate lift training systems comprises a belt mounted goniometer which is operatively coupled to a microprocessor having an electronic memory for time logging a lifting session. To insure actual usage the belt is also provided with temperature and/or motion sensors.

U.S. Pat. No. 5,749,838 discloses a posture training device, which includes a frame and a module floatingly engaged with the frame. The device can be held snugly against the backbone of a person by a belt or garment, such that an increase in curvature of the backbone in either the midsagittal plane or a transverse plane moves the module relative to the frame. When the module has been moved sufficiently to indicate a poor posture position, a tactile signal generator within the module is activated to vibrate, thereby alerting the person that he or she has assumed a poor posture.

U.S. Pat. No. 6,059,576 discloses an electronic device, system, and method to monitor and train an individual on proper motion during physical movement. The system employs an electronic device which tracks and monitors an individual's motion through the use of an accelerometer capable of measuring parameters associated with the individual's movement. The device also employs a user-programmable microprocessor which receives, interprets, stores and responds to data relating to the movement parameters based on customizable operation parameters, a real-time clock connected to the microprocessor, memory for storing the movement data, a power source, a port for downloading the data from the device to other computation or storage devices contained within the system, and various input and output components. The downloadable, self-contained device can be worn at various positions along the torso or appendages being monitored depending on the specific physical task being performed. The device also detects the speed of movements made while the device is being worn. When a pre-programmed recordable event is recognized, the device records the time and date of the occurrence while providing feedback to the wearer via visual, audible and/or tactile warnings.

U.S. Pat. No. 4,665,928 discloses a range of motion measuring and displaying device, which includes a modular housing containing a micro-computer and associated circuitry as well as input controls, display and printout facilities, input and output cord connections and a software receiving area which is provided so as to detachably connect to the modular housing diverse programs enabling diverse modes of operation of the invention. One of the cord connections is provided for attachment thereto of the cord of an electronic goniometer which has been designed specifically to interface with the modular housing. The electronic goniometer is of the variable resistance type and outputs voltages interpretable by the micro-computer which voltages are indicative of a rotation of the electronic goniometer with respect to an original vertical position. In one embodiment of the present invention, the modular housing has cord connections for a plurality of such electronic goniometers which may be used simultaneously in the operation of the present invention so as to determine the range of motion of a plurality of joints with respect to one another, such as separate vertabral joints of the spinal column. The present invention is usable to measure the range of motion of the various joints of the human body in any desired sequence and includes a separate mode enabling the performance of sets and repetitions of various exercises with the various body joints with the micro-computer monitoring such exercises.

U.S. Patent Application No. 20020170193 discloses a sensing device, which is attached to a living subject that includes sensors for distinguishing lying, sitting, and standing positions. In another embodiment, sensor data is stored in a storage device as a function of time. Multiple points or multiple intervals of the time dependent data are used to direct a feedback mechanism to provide information or instruction in response to the time dependent output indicating too little activity, too much time with a joint not being moved beyond a specified range of motion, too many motions beyond a specified range of motion, or repetitive activity that can cause repetitive stress injury.

There is a need, however, for a device that can be attached to a person to retrain his bending habits by consistently alerting him when he is jeopardizing his lower back by bending over too much at the waist and to record how many times in a given period the person has bent over too far at the waist. The previously cited art fails to provide a device that not only alerts a patient when he has bent at the waist past a set point which he sets to indicate the maximum amount that he is supposed to bend, but also tracks the number of times over a given period that the person has been alerted. It also displays the amount in degrees that a person is bending at any particular time. The set point can be set based on a certain body position, or a certain numeric degree of bend as indicated by the LCD readout. It would therefore be beneficial if a device existed, as a retraining aid, which detected when a person bent past a certain set point beyond which he is not supposed to bend, and recorded the number of times the person has thus triggered the set point alarm.

OBJECTS AND SUMMARY OF THE INVENTION

It is an object of the present invention to provide a back training device that will alert a person when he or she bends over at the waist.

It is a further object of the present invention to provide a back training device that includes a control box; a detector mounted inside the control box, for detecting when a person bends at the waist beyond a set point; and an alert means, operatively connected to the detector for alerting the person when the person bends at the waist beyond the set point.

It is yet a further object of the present invention to provide a miniature back training device such that the miniature back training device can be attached by an adhesive patch to the person, so that a belt is not needed to attach the device to the person.

It is yet a further object of the present invention to provide a back training device that utilizes a goniometer to detect when the person bends at the waist.

In accordance with a first aspect of the present invention, a novel back training device is disclosed. The novel back training device includes a control box; a detector mounted inside the control box, for detecting when a person bends at the waist beyond a set point; and an alert means, operatively connected to the detector for alerting the person when the person bends at the waist beyond the set point.

In accordance with another aspect of the present invention, a novel miniature training device is disclosed. The novel miniature training device includes a miniature control box; a miniature detector, for detecting when a person bends beyond a set point at the waist; and a miniature alert means, operatively connected to the detector for alerting the person when the person bends beyond the set point at the waist. The miniature detector and/or alert means are adapted to be directly attached to the skin of the person and in communication with the miniature control box.

In accordance with yet another aspect of the present invention, a novel back training device utilizing a goniometer is provided. The novel back training device utilizing a goniometer includes a goniometer for sensing when a person bends at the waist; and an alert means, operatively connected to the goniometer for alerting the person when the person bends at the waist.

BRIEF DESCRIPTION OF THE DRAWINGS

The foregoing summary, as well as the following detailed description of a preferred embodiment of the present invention will be better understood when read with reference to the appended drawings, wherein.

DETAILED DESCRIPTION OF THE PREFERRED EMBODIMENT

Figure 1:
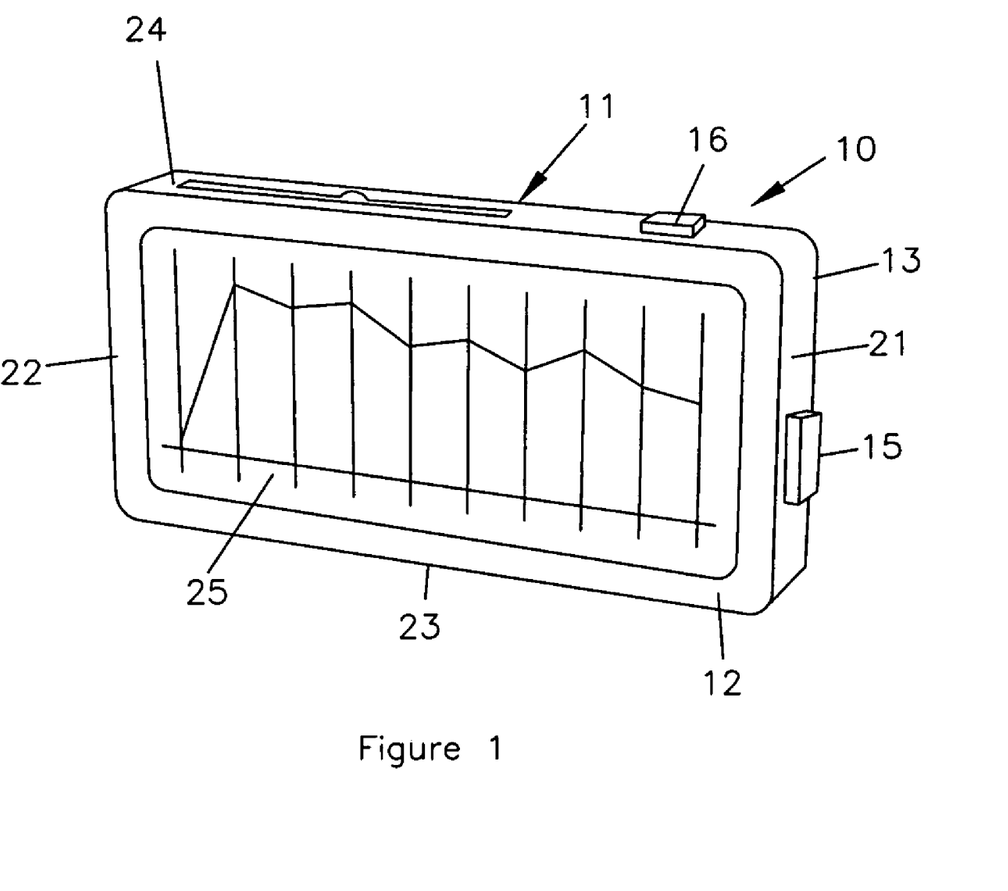
FIG. 1 is a perspective view of a back training device in accordance with the present invention.
Figure 2:
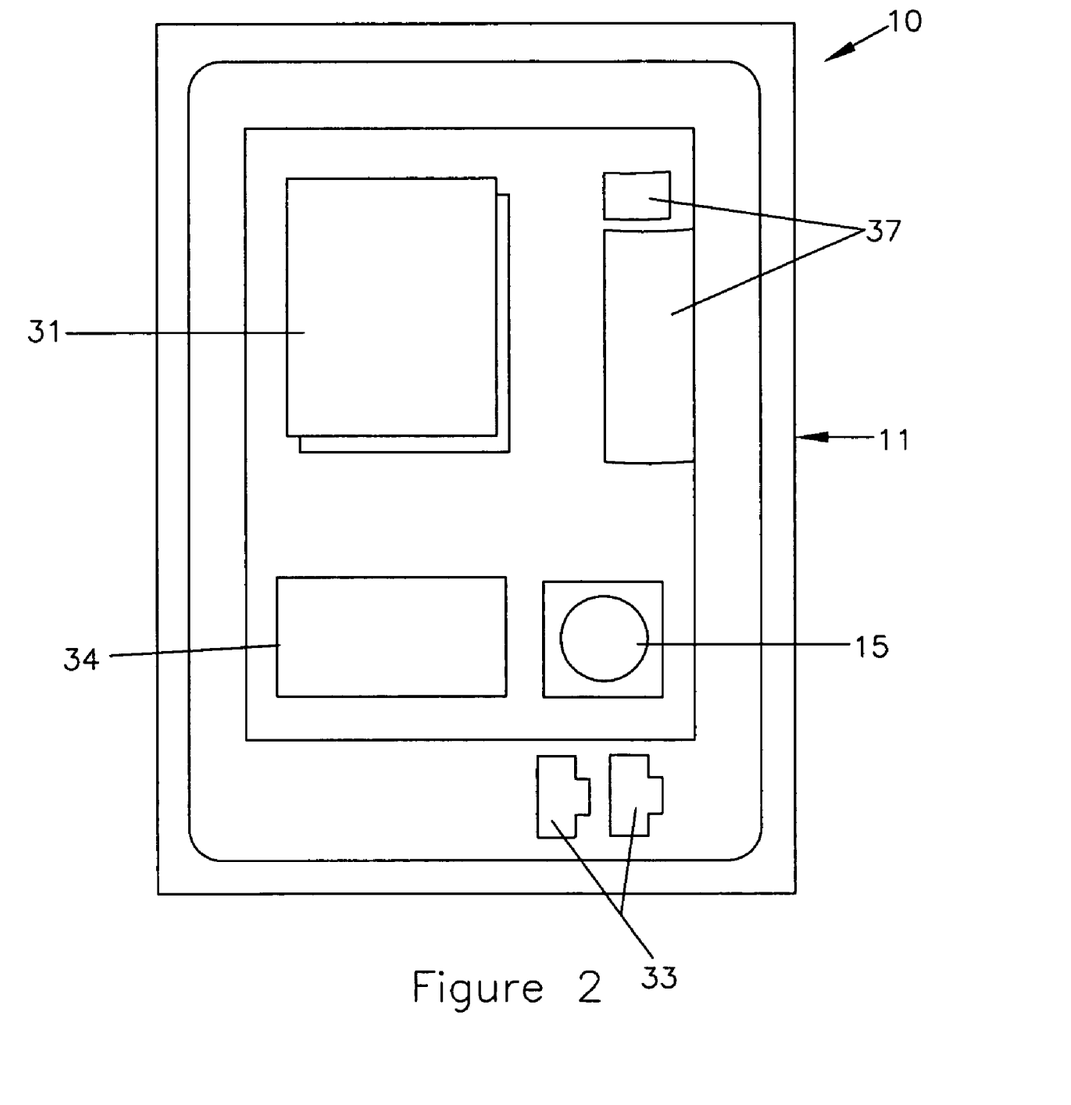
FIG. 2 is an internal side elevation schematic of the back training device of FIG. 1.

Referring now to the drawings, wherein like reference numerals refer to the same components across the several views and in particular to FIGS. 1 and 2, there is shown a back training device 10. The back training device 10 includes a control box 11, having a first side 12, a second side 13, a first edge 21, a second edge 22, a third edge 23, and a fourth edge 24.

The control box 11 has a display 25 mounted on the first side 12 of the control box 11. In a preferred embodiment of the present invention, the display 25 is a liquid crystal display (LCD), however, any type of display known to one of ordinary skill in the art may be utilized as display 25. As depicted in FIG. 1, the display 25 is a graphing display, however, the display can be of any type known to one of ordinary skill in the art, for example, a numeric display. A set button 15 is mounted on the first edge 21 of the control box 11. A detector 31 is mounted in the control box 11 for detecting when a person bends beyond a certain set point. In a preferred embodiment of the present invention, the detector 31 is disposed within the control box 11, however, the detector may be mounted to the control box 11 anywhere known to one of ordinary skill in the art. Additionally, in a preferred embodiment of the present invention the detector 31 is a Micro Electromechancial System (MEMS), however any detector known to one of ordinary skill in the art may be employed. Operatively connected to the detector 31 is an alert means 37. The set button 15 is also operatively connected to the detector 31 to set the range of motion for the detector 31. Also included in the control box 11 is logic/counter memory chip 34. The logic/counter memory chip 34 stores the number of times that the person bends at the waist beyond the set point set by the set button 15. In a preferred embodiment of the present invention, the logic/counter memory chip 34 stores the number of times the person bent at the waist beyond the set point in a 24 hour period, however, any period known to one of ordinary skill in the art may be used, such as a period of 30 days, or months.

For example, in a preferred embodiment of the invention, the person may bend over to an allowable angle, and then press the set button 15. The detector 31 will then be set to allow the person to bend at the waist until he goes beyond the set point. When the person bends beyond the set point that the detector 31 is set via the set button 15, the detector 31 will activate the alert means 37. In a preferred embodiment of the present invention, the alert means 37 is a buzzer, beeper, or vibrator. However, any alert means 37 known to one of ordinary skill in art may be employed to alert the person that he or she has bent over beyond the set point set for detector 31 by the set button 15.

A power source 33 is included in the control box 11 of the back training device 10 to provide power to the components that require it. For example, in a preferred embodiment of the present invention, the power source 33 provides power to the detector 31, the alert means 37, and the logic/counter memory chip 34. However, any component known to one of ordinary skill in the art can be connected to the power source 33, and some components known to one of ordinary skill in the art that do not require power can be unconnected to the power source 33. For example, the detector 31 could be a mechanically operated type detector 31, and therefore not require connection to the power source 33. In a preferred embodiment of the present invention, the power source 33 is at least one battery, however, any known power source 33 known to one of ordinary skill in the art may be utilized, including additional batteries.

The logic/counter memory chip 34 counts the number of times the detector 31 detects the person bend beyond the set point set by the set button 15, and the degree of bend. The number of times stored, and the degree of bend, can be accessed via the display 25. Referring again to FIG. 1, the fourth side 24 of the control box 11 of the back training device 10 includes a display button 16. The display button 16 is operatively connected to the display 25 and allows the person to utilize various functions on the display 25. For example, the display button 16 may be programmed to allow the person to scroll the dates and events along the display 25. The display button 16 and the display 25 would also have to be operatively connected to the logic/counter memory chip 34 in order to allow the display to scroll through the information regarding the number of times and dates that the person bent past the set point set in the detector 31. The display 25 can display the information as a graph from day to day or it can be a numerical/digital display wherein the display 25 displays only the numeric information of the number of times and dates.

The back training device 10 can be worn by the person in a variety of ways. For example, the back training device 10 can be mounted on the person by means of a strap, belt, or adhesive tape. Additionally, the back training device 10 may be placed in a holster which could be worn by the person. A belt clip alone or in concert with a holster can be used to house the back training device 10.

Figure 3:
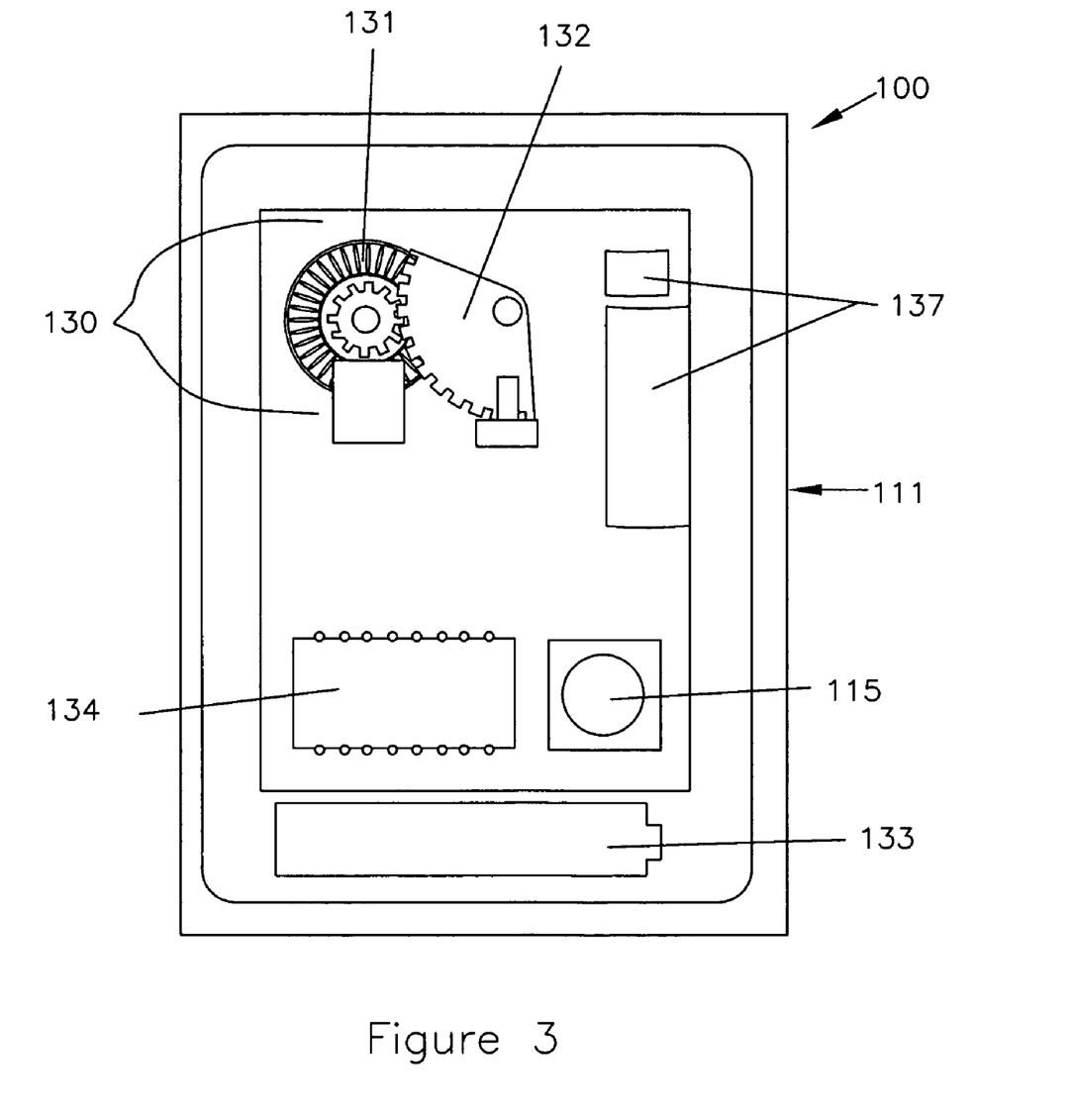
FIG. 3 is an internal side elevation schematic of an alternative embodiment of a back training device in accordance with the present invention.

Referring now to FIG. 3, an internal side elevation schematic of an alternative embodiment of a back training device 100 is shown. The back training device 100 includes a control box 111.

The control box 111 has a display (not shown) mounted on the control box 111. In a preferred embodiment of the present invention, the display is a liquid crystal display (LCD), however, any type of display known to one of ordinary skill in the art may be utilized as the display. In general, the control box 111 of the back training device 100 is very similar to the control box 11 of the back training device 10. The display of the back training device 100 is similar to the display 25 of the back training device 10 in that it is a graphing display in a preferred embodiment. However, the display can be of any type known to one of ordinary skill in the art, for example, a numeric display. A set button 115 is mounted on the control box 111 much the same way that the set button 15 is mounted on the control box 11 of the back training device 10. A goniometer detector 130 is mounted in the control box 111 for detecting when a person bends beyond a certain set point. The goniometer detector 130 includes in one embodiment of the present invention an optical indexer 131 and a weight and drive gear 132. Operatively connected to the goniometer detector 130 is an alert means 137. The set button 115 is also operatively connected to the goniometer detector 130 to set the set point for the goniometer detector 130. Also included in the control box 111 is a logic/counter memory chip 134. Both the goniometer detector 130 and the set button 115 may be operatively connected to the logic/counter memory chip 134 to set the set point for the goniometer detector 130. For example, in a preferred embodiment of the invention, the person may bend over to an allowable angle, and then press the set button 115. The goniometer detector 130 will then be set to allow the person to bend over up to that set point. When the person bends beyond the set point that the goniometer detector 130 is set to via the set button 115, the goniometer detector 130 will activate the alert means 137. In a preferred embodiment of the present invention, the alert means 137 is a buzzer, beeper, or vibrator. However, any alert means 137 known to one of ordinary skill in the art may be employed to alert the person that he or she has bent over beyond the set point set for goniometer detector 130 by the set button 115.

A power source 133 is included in the control box 111 of the back training device 100 to provide power to the components that require it. For example, in a preferred embodiment of the present invention, the power source 133 provides power to the alert means 137, the logic/counter memory chip 134. However, any component known to one of ordinary skill in the art can be connected to the power source 133, and some components known to one of ordinary skill in the art that do not require power can be unconnected to the power source 133. In a preferred embodiment of the present invention, the power source 133 is at least one battery, however, any known power source 133 known to one of ordinary skill in the art may be utilized, including additional batteries.

The logic/counter memory chip 134 counts the number of times the goniometer detector 130 detects the person bend beyond the set point set by the set button 115. The number of times is stored and can be accessed via the display. The control box 111 of the back training device 100 includes a display button (not shown). The display button is operatively connected to the display and allows the person to utilize various functions on the display. For example, the display button may be programmed to allow the person to scroll the dates and events along the display. The display button and the display would also have to be operatively connected to the logic/counter memory chip 134 in order to allow the display to scroll through the information regarding the number of times and dates that the person bent past the range set in the goniometer detector 130, as well as the degree of bend. The display can display the information as a graph from day to day or it can be a numerical/digital display wherein the display displays only the numeric information of the number of times and dates.

Figure 4A:
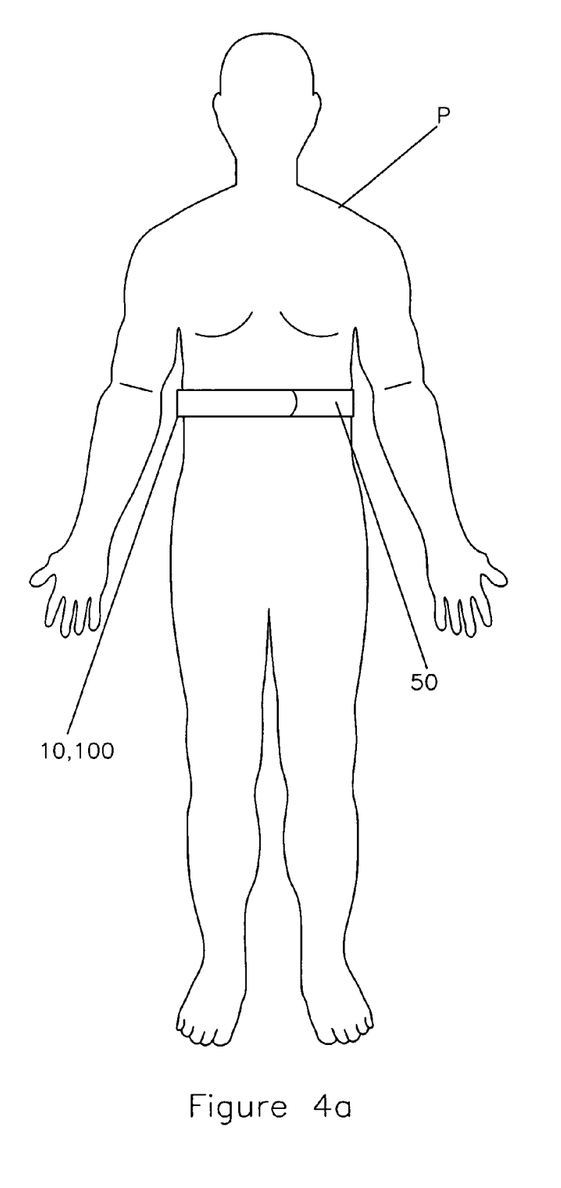
FIG. 4A is a front elevation view of a person wearing the back training device in accordance with the present invention.
Figure 4B:
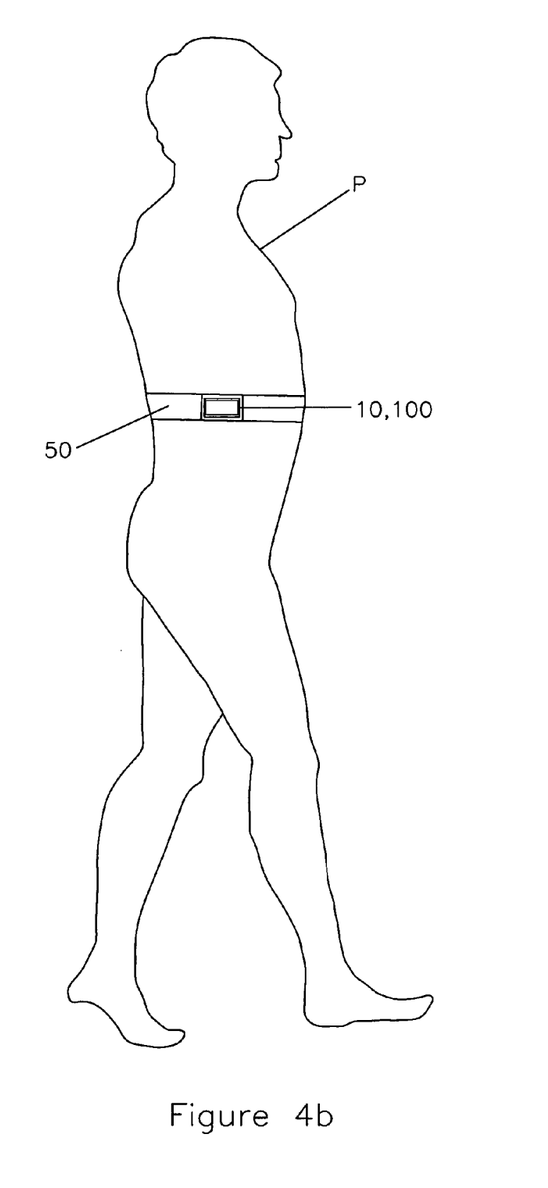
FIG. 4B is a side elevation view of the person wearing the back training device in accordance with the present invention.

Referring now to FIGS. 4A and 4B, the back training device 100 is shown mounted on a person P. The back training device 10 can be mounted in similar fashion. The back training device 10 or 100 is attached to a strap 50, and is placed on the side of the person P's body. In a preferred embodiment of the present invention, the back training device 10 or 100 is placed on the right side of the person P. However, the back training device 10 or 100 can be placed on the person P wherever one of ordinary skill in the art can see fit, including the left side.

In an additional embodiment of the present invention, the back training device can be in miniature form, and can be utilized for training other areas of the body in addition to the back. In this way, the miniature detector of the miniature training device can be directly attached to the body of the person P, without the use of a belt, strap, and the like. The miniature control box in this embodiment is separate from the miniature detector. An adhesive patch may be employed to hold the miniature detector of the miniature training device onto the skin of the person, however the miniature detector may also be attached to the person by other means, such as by the use of a strap, belt, and the like.

A display is included on the control box, and in a preferred embodiment, the miniature alert means is included in the control box. Although in a preferred embodiment of the present invention, the miniature control box is a key fob which can be carried in the pocket of the person wearing the miniature training device, various other means of carrying the miniature control box may be employed. For example, the miniature control box may be attached to the person by means of a belt clip, or any other attachment means known to one of ordinary skill in the art. A power source is required for the miniature control box, miniature alert means and miniature detector. The miniature detector, in a preferred embodiment of the present invention can be either a strain gauge or a MEMS chip, however any miniature detector known to one of ordinary skill in the art may be used as the miniature detector for the miniature training device. The miniature strain gauge device of the miniature training device could be placed at the base of the spine for detection. However, when the miniature detector is in the form of a MEMS chip, the miniature detector would have to be placed on either side of the body in order to register a bend. In this fashion, the miniature detector could be attached directly to the skin or held by a belt, strap, clip, and the like.

The miniature training device could also be used for retraining other areas of the body such as the neck. For example, the miniature strain gauge of the miniature training device could be placed at the base of the back of the neck, to retrain a person who is bending too far at the neck. The miniature strain gauge is epoxied to a thin plastic piece to be attached to the skin of the person, however any material known to one of ordinary skill in the art may be used, such as a thin metal piece, and the like. In the embodiment of the miniature training device where the miniature detector is a MEMS chip, the miniature detector would be placed on either side of the neck, preferably in an area where it will register the most bend in the neck, such as the middle of the neck between the base of the neck and the head.

The miniature training device includes all other components of the back training device 10 in miniature form. For example, a miniature logic/memory chip is included in the miniature training device and may be included in the miniature control box. Since the miniature detector is sometimes separate from the miniature alert means and the miniature control box, means for communicating between each other is required. In a preferred embodiment of the present invention, the miniature detector communicates wirelessly with the miniature control box, for example via a radio signal, however any means of communication known to one of ordinary skill in the art may be utilized.

Figures 5A, 5B:
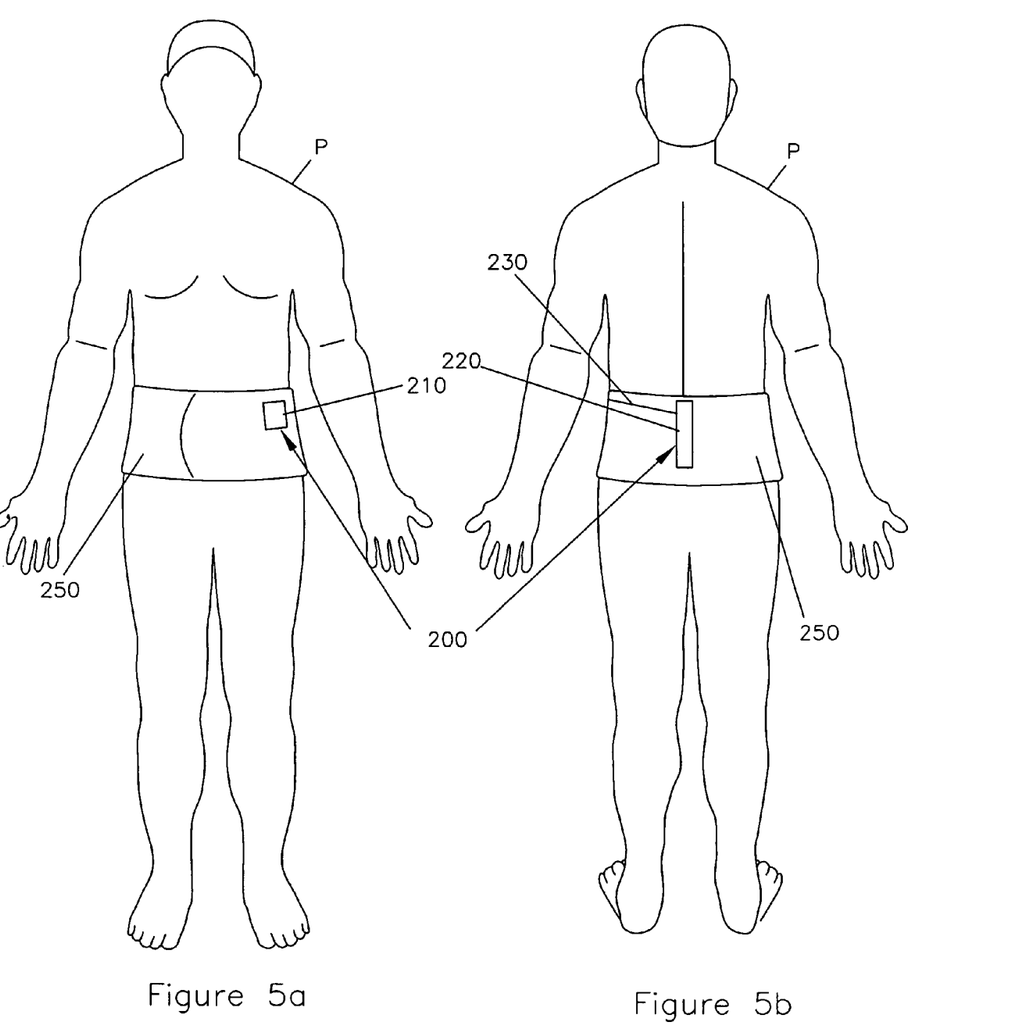
FIG. 5A is a front elevation view of a person wearing an alternative embodiment of the back training device in accordance with the present invention.
FIG. 5B is a rear elevation view of the person wearing the alternative embodiment of the back training device in accordance with the present invention.

Referring now to FIGS. 5A and 5B, another alternative embodiment of a back training device 200 is depicted. The back training device 200 includes a control box 210 and a detector 220. The control box 210 is similar to the control boxes 11 and 111, however, the control box 210 does not include a detector. The detector 220 is a strain gauge in a preferred embodiment of the present invention, however any known detector to one of ordinary skill in the art may be utilized as detector 220. The detector 220 is connected to the control box 210 via means of a wire 230, and is worn at the base of the spine of the person. Additionally, the detector 220 could be in wireless communication with the control box 210, in which case the wire 230 would not be needed. Both the control box 210 and the detector 220 of the back training device 200 are typically mounted on a person P' via a belt 250. Although in a preferred embodiment of the present invention, the belt 250 is a wide belt, any size known to one of ordinary skill in the art may be used. The detector 220, in a preferred embodiment, is epoxied to a thin plastic or metal piece which is placed on the body of the person P'.

All the embodiments of the present invention, including the back training device 10, 100, 200, and the miniature back training device will include an interface to connect the device to a computer and the like. In a preferred embodiment of the present invention, the interface will include a Universal Serial Bus (USB) interface. However, any known means to one of ordinary skill in the art, of communicating from the back training device to the computer may be employed, such as Firewire, wireless infrared, and the like. In this manner, the data stored in the back training device can be uploaded into a computer for further study.

In view of the foregoing disclosure, some advantages of the present invention can be seen. For example, a novel back training device is disclosed. The novel back training device attaches to a person and alerts the person when he or she bends beyond an acceptable limit. The device further includes a means to record the number of times the person bends beyond his or her set point, and how many times it happened over a period of time, such as 24 hours.

While the preferred embodiment of the present invention has been described and illustrated, modifications may be made by one of ordinary skill in the art without departing from the scope and spirit of the invention as defined in the appended claims. For example, instead of an optical indexer and weight and drive gear, a Micro Electromechanical System (MEMS) may be employed. The MEMS unit would operate to detect when the person bends beyond the set point set on the detector. Additionally, in a preferred embodiment of the present invention, the detector may be a strain gauge, however any detector known to one of ordinary skill in the art may be utilized. Additionally, the strain gauge may be separate from the control box, by being attached, preferably epoxied, to a thin plastic piece which would be held by a belt, strap, or other device to the body of the person.

What is claimed is:

1. A back training device, comprising:
a portable control box;
a detector mounted to the portable control box for detecting when a person bends at the waist beyond a user selectable set point and for measuring a number of degrees associated with how far the person bends at the waist, wherein the detector is configured to be worn by the person such that the detector is positioned upon the person's body to measure bending at the waist;
a set button mounted on the portable control box and operatively connected to the detector for setting the user selectable set point, wherein the person sets a user selectable set point while wearing the detector by bending over to a maximum desired angle and by pressing the set button while being bent over to the maximum desired angle, such that the user selectable set point is defined as the maximum desired bending angle of the person;
an alert means operatively connected to the detector and mounted to the portable control box for alerting the person each time the person bends at the waist beyond an alert point, wherein the alert point is the same as the user selectable set point, such that the alert means alerts the user each time the user bends beyond the user selectable set point, thereby providing negative feedback to the person each time the person bends at the waist beyond the user selectable set point, thereby training the person to refrain from bending beyond the user selectable set point, wherein the alert means is activated by the detector when it is detected that the person has bent at the waist beyond the user selectable set point;

a memory configured to store data corresponding to when the person bends at the waist beyond the user selectable set point, wherein the memory is configured to function as a logic/counter storage device, wherein data is stored each time the person bends at the waist beyond the user selectable set point, the stored data comprising a date, a time, and the number of degrees associated with how far the person bends at the waist;

a display operatively connected to the detector configured to display data stored by the memory; and a processor operatively connected to the memory and the display to facilitate the display of data stored by the memory.

2. The device of claim 1, wherein the detector is housed within the portable control box.

3. The device of claim 1, wherein the alert means includes a power source, wherein the power source is electrically connected to the alert means for powering the alert means.

4. The device of claim 3, wherein the alert means is a vibrator.

5. The device of claim 3, wherein the alert means is a buzzer.

6. The device of claim 3, wherein the power source includes at least one battery.

7. The device of claim 3, further comprising a display button for browsing the display output, the display being connected to the power source.

8. The device of claim 1, wherein the display includes a liquid crystal display readout.

9. The device of claim 8, wherein the display displays the date and time that the detector detected the person bending beyond the set point at the waist.

10. The device of claim 1, wherein the display includes a liquid crystal screen.

11. The device of claim 10, wherein the memory automatically stores and the display automatically displays a graph of the number of times that the detector detected the person bending beyond the set point at the waist over a period of time, and the degree of bend.

12. The device of claim 11, wherein the period of time is 30 days.

13. The device of claim 11, wherein the period of time is 24 hours.

14. The device of claim 1, further comprising a strap, which holds the device to the person.

15. The device of claim 14, wherein the strap is worn directly on the skin, under the clothing.

16. The device of claim 1, wherein the device is mounted within a holster worn by the person.

17. The device of claim 1, wherein the detector includes a strain gauge.

18. The device of claim 17, wherein the device includes a thin plastic piece wherein the strain gauge is attached to the surface of the thin plastic piece and is held against the body of the person.

19. The device of claim 17, wherein the device includes a thin metal piece wherein the strain gauge is attached to the surface of the thin metal piece and is held against the body of the person.

20. The back training device of claim 1, wherein the portable control box comprises a computer interface.

21. The back training device of claim 1, wherein setting the user selectable set point comprises:

the person wearing the detector bending at the waist to a desired angle; and activating the set button mounted on the portable control box while the person is bending at the waist to the desired angle, the user selectable set point defining a bending angle at the person's waist when the set button is activated.

22. A back training device, comprising:

a portable control box;

a detector mounted external to, and operatively connected to, the portable control box for detecting when a person bends at the waist beyond a set point and for measuring a number of degrees associated with how far the person bends at the waist, wherein the detector is adapted to be worn by the person, wherein the detector is selected from the group consisting of a Micro Electromechanical System, a goniometer, and a strain gauge;

an alert means, mounted within the portable control box, operatively connected to the detector for alerting the person each time the person bends at the waist beyond the set point, wherein the detector activates the alert means when the detector detects that the person has bent over beyond the set point;

a set button mounted on the portable control box and operatively connected to the detector for setting the set point, wherein the person sets the set point while the person is wearing the detector by bending over to a maximum desired angle and by pressing the set button while the person is bent over to the maximum desired angle, wherein the set point is defined as the position of the user when the user presses the set button, wherein the set point is selectively set by the person wearing the detector such that the alert means is activated each subsequent time the person bends at the waist beyond the set point;

a display operatively connected to the portable control box and being adapted to display information relating to the person bending beyond the set point during a specified time period; and a display button operatively connected to the display for browsing the displayed information and enabling selection of a desired time period.

23. The back training device of claim 22, wherein the detector comprises a strain gauge.

24. The device of claim 23, wherein the strain gauge is epoxied to a thin piece of plastic which is directly attached to the skin of the person.

25. The device of claim 23, wherein the strain gauge is epoxied to a thin piece of metal which is directly attached to the skin of the person.

26. The back training device of claim 23, further comprising a wire connecting the strain gauge to the alert means within the control box.

27. The back training device of claim 23, wherein the strain gauge is in wireless communication with the alert means within the control box.

28. The back training device of claim 26 or 27, further comprising a belt worn by a person, wherein the control box, strain gauge and wire are mounted on the belt.

29. The back training device of claim 28, wherein the belt has a width greater than twice the width of the control box.

30. The back training device of claim 28, wherein the strain gauge is worn at the base of the spine of the person.

31. The device of claim 22, wherein the alert means includes a power source, and a logic/counter memory chip, wherein the power source is electrically connected to the logic/counter memory chip and the alert means for powering the alert means and the logic/counter memory chip.

32. The device of claim 31, wherein the alert means is a vibrator.

33. The device of claim 31, wherein the alert means is a buzzer.

34. The device of claim 31, wherein the power source includes at least one battery.

35. The device of claim 31, wherein the display is connected to the power source.

36. The device of claim 35, wherein the display includes a liquid crystal display readout.

37. The device of claim 36, wherein the display displays the date and time that the detector detected the person bending beyond the set point at the waist, and the degree of bend.

38. The device of claim 35, wherein the display includes a liquid crystal screen.

39. The device of claim 38, wherein the display automatically records and graphs the number of times that the detector detected the person bending beyond the set point at the waist over a period of time, and the degree of bend.

40. The device of claim 39, wherein the period of time is 30 days.

41. The device of claim 39, wherein the period of time is 24 hours.

42. The back training device of claim 22, wherein the set point corresponds to the bending angle of the person when the set button is pressed.

43. The back training device of claim 22, wherein setting the set point comprises:
the person wearing the detector bending at the waist to a desired angle; and
activating the set button mounted on the portable control box while the person is bending at the waist to the desired angle, the set point defining a bending angle at the person's waist when the set button is activated.

44. A body movement training device, comprising:
a detector configured to measure the bending angle at a designated location on a user's body and to detect when the user bends beyond a set point; and
a portable control mechanism in communication with the detector, the portable control mechanism comprising:
a set button mounted on the portable control mechanism for setting the set point, the set button being operatively connected to the detector to set the range of motion for the detector, wherein the user sets the set point while wearing the detector by bending the designated location on the user's body to a maximum desired angle and by pressing the set button while the person is bent to the maximum desired angle, wherein the set point is defined as the bending angle of the user when the user presses the set button, wherein the set point is set by bending the designated location to the set point and pressing the set button;
an alerting device configured to alert the user each time the user bends the designated location beyond an alert point, wherein the alert point is the same as the set point, such that the alerting device alerts the user each time the user bends the designated location beyond the bending angle defining the set point, the alerting device being operatively connected to the detector such that the alerting device is activated by the detector each time the detector detects that the user has bent the designated location beyond the set point, thereby providing negative feedback to the user each time the user bends the designated location beyond the set point;
a monitoring device configured to record the number of times the user bends beyond the set point and the corresponding bending angles, the monitoring device comprising a memory;
a computer interface for connecting the control mechanism to a computer; and
a display for displaying data recorded by the monitoring device, wherein the display is adapted to enable the user to selected a desired time period and view on the display the data recorded by the monitoring device for the selected time period.

45. The body movement training device of claim 44, further comprising a wireless connection that facilitates communication between the detector and the portable control mechanism.

46. The body movement training device of claim 44, further comprising a wired connection that facilitates communication between the detector and the portable control mechanism.

47. The body movement training device of claim 44, wherein the detector is attached to the portable control mechanism.

48. The body movement training device of claim 44, wherein the display is configured to display the date and time the user bends beyond the set point and the corresponding bending angle.

49. The body movement training device of claim 44, wherein the display is configured to graph data related to the number of times the user bends beyond the set point.

50. The body movement training device of claim 44, in which the computer interface is one of a USB interface or a firewire interface.

51. The body movement training device of claim 44, wherein the display is an LCD display.

52. A back training device configured to be worn by a user with the aid of a strap, belt, holster, or adhesive tape, the back training device comprising:
a detector configured to measure a degree of bend at the user's waist and to detect when the user bends beyond a user selectable set point, wherein the detector is selected from the group consisting of a Micro Electromechanical System, a goniometer, and a strain gauge;
a portable control box in communication with the detector, the portable control box comprising:
a set button mounted on the portable control box for inputting the set point, the set point being a user defined degree of bend at the user's waist, the set button being operatively connected to the detector to set the range of motion for the detector, wherein the user sets the set point while wearing the detector by bending over at the waist to a maximum desired angle and by pressing the set button while being bent at the waist to the maximum desired angle, thereby defining the set point as the position of the user's body when the set button is pressed, wherein the set point is set by bending over to the set point and pressing the set button;
an alerting device configured to alert the user when the user bends beyond an alert point, the alert point being the same as the set point such that the alerting device alerts the user when the user bends beyond the set point, the alerting device being operatively connected to the detector such that the alerting device is activated by the detector each time the detector detects that the user has bent over beyond the set point, thereby providing negative feedback to the user each time the user bends beyond the set point, wherein the alerting device is selected from the group consisting of a buzzer, a beeper, and a vibrator;
a memory configured to store information relating to the user bending beyond the set point, the information comprising the number of times the user bends at the waist beyond the set point set by the set button and the corresponding degree of bend at the user's waist, wherein the memory comprises a logic/counter memory chip adapted to store the information according to a plurality of time period;

a display operatively connected to the memory and configured to display the date and time the user bends beyond the set point and the corresponding degree of bend at the user's waist, the display being configured to numerically and graphically display information relating to the user bending beyond the set point, wherein the display is adapted to display the information relating to the user bending beyond the set point over the plurality of time periods;

a display button operatively connected to the display and the memory, wherein the display button allows the user to browse display output and select a desired time period from the plurality of time periods in order to view on the display information relating to the user bending beyond the set point during the selected time period;

a computer interface adapted to facilitate communication of the stored information between the portable control box and an external computer, the computer interface being selected from the group consisting of a USB interface, a Firewire interface, and a wireless interface;

a power source adapted to provide power to at least one of the detector, the alert means, the memory, and the display.

53. The back training device of claim 52, further comprising a wireless connection that facilitates communication between the detector and the portable control box.

54. The back training device of claim 52, further comprising a wired connection that facilitates communication between the detector and the portable control box.

55. The back training device of claim 54, wherein the detector is attached to the portable control box.

56. The back training device of claim 52, wherein the display graphs the number of times the user bends beyond the set point and the corresponding degrees of bend at the user's waist.

57. The back training device of claim 52, wherein the portable control box is mounted within a holster worn by the user proximate the user's hip.

58. The back training device of claim 52, wherein the detector is coupled to a strap that is worn proximate the user's skin.

59. The back training device of claim 52, wherein the set point corresponds to a bending position of user when the set button is pressed.

60. The back training device of claim 52, wherein setting the set point comprises:

the user wearing the detector bending at the waist to a desired angle; and activating the set button mounted on the portable control box while the user is bending at the waist to the desired angle, the set point defining a bending angle at the user's waist when the set button is activated.

61. A method for monitoring back movement, the method comprising:

providing a back training device comprising:

a detector configured to measure the degree of bend at a user's waist and to detect when the user bends beyond a user selectable set point; and a portable control mechanism operatively connected to the detector, wherein the detector is mounted on the portable control mechanism;

positioning the detector on the user's body;

setting the user selectable set point, wherein setting the user selectable set point comprises:

the user bending at the waist to a desired angle to define the user selectable set point; and activating a set button mounted on the portable control mechanism while the user is bending at the waist to the desired angle, the user selectable set point defining a bending angle at the user's waist when the set button is activated;

providing an alert to the user each time the user bends beyond an alert point to inform the user that the user has bent beyond the alert point, wherein the alert point is the same as the user selectable set point such that the alert is provided each time the user bend beyond the user selectable set point;

monitoring when the user bends beyond the user selectable set point; and displaying on a display operatively connected to the control mechanism the number of times the user bends beyond the user selectable set point.

62. The method of claim 61, further comprising connecting the portable control mechanism to a computer, the portable control mechanism comprising a computer interface chosen from one of a USB interface or a firewire interface.

* * * * *